United States Patent

Yurugi et al.

[11] 3,948,908
[45] Apr. 6, 1976

[54] PYRIDOPYRIDAZINE DERIVATIVES

[75] Inventors: Shojiro Yurugi, Senbonmaruta; Shintaro Kikuchi, Takarazuka, both of Japan

[73] Assignee: Takeda Chemical Industries, Ltd., Osaka, Japan

[22] Filed: Dec. 15, 1972

[21] Appl. No.: 315,315

[30] Foreign Application Priority Data
Dec. 28, 1971 Japan.................................. 47-1253

[52] U.S. Cl..................... 260/246 B; 260/247.5 DP; 260/250 AC; 424/250; 424/248
[51] Int. Cl.²........................................ C07D 295/00
[58] Field of Search . 260/247.5 DP, 250 AC, 246 B

[56] References Cited
UNITED STATES PATENTS

| | | | |
|---|---|---|---|
| 3,186,991 | 6/1965 | Ohnacker | 260/247.5 B |
| 3,248,395 | 4/1966 | Ohnacker | 260/247.5 B |
| 3,296,251 | 1/1967 | Bell et al. | 260/234.3 |
| 3,454,557 | 7/1969 | Patchett et al. | 260/239.1 |
| 3,622,569 | 11/1971 | Lemieux | 260/239.1 |
| 3,711,476 | 1/1973 | Diebold et al. | 260/244 R |
| 3,749,717 | 7/1973 | Haugwitz et al. | 260/243 R |
| 3,764,598 | 10/1973 | Yurgi et al. | 260/246 B |

OTHER PUBLICATIONS
Matsuo et al., J. of the Pharm. Soc. of Japan, Vol. 92, No. 6, pp. 703–707 (June 1972).

*Primary Examiner*—Lorraine A. Weinberger
*Assistant Examiner*—Killos
*Attorney, Agent, or Firm*—Wenderoth, Lind & Ponack

[57] ABSTRACT

A pyrido [3,4-d] pyridazine derivative is provided herein of the formula:

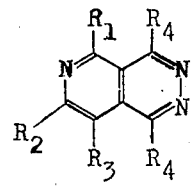

wherein $R_1$ is hydrogen or an alkyl group of 1 to 4 carbon atoms; $R_2$ is an alkyl group of 1 to 4 carbon atoms, an aralkyl group of 7 to 8 carbon atoms, or a substituted or unsubstituted phenyl, naphthyl, furyl or pyridyl, the substituent being a lower alkoxy group of 1 to 3 carbon atoms, a lower alkyl group of 1 to 3 carbon atoms, halogen or nitro; $R_3$ is hydrogen or a lower alkoxy group of 1 to 4 carbon atoms; and $R_4$ is a substituted or unsubstituted morpholino, piperidino or pyrrolidino, the substituent being methyl or ethyl and a pharmaceutically acceptable salt thereof. The compounds of the present invention have effective and strong diuretic action and exhibit extremely low toxicity characteristics.

8 Claims, No Drawings

PYRIDOPYRIDAZINE DERIVATIVES

The present invention relates to novel pyrido[3,4-d]-pyridazine derivatives which have effective diuretic action.

There have been synthesized many kinds of diuretics, and some of them have been applied in practice, typical examples of which are chlorothiazide derivatives, acetazolamide, triamterene, trifrocine, furosemide, etc.

However, known diuretics are not very satisfactory in view of one or more of such disadvantages as promoting the excretion of potassium as well as sodium, causing side effects (e.g. increase of blood glucose level and blood uric acid level) upon long-term administration, and showing rather low diuretic activity and rather high toxicity.

The present inventors have sought to provide an effective diuretic which is unaccompanied by such disadvantages.

Accordingly, the present inventors have synthesized novel pyrido[3,4-d]pyridazine derivatives, and found out that these compounds are useful as effective and improved diuretics.

The present invention has been accomplished on the basis of this finding.

Thus, the principal object of the present invention is to provide novel pyrido[3,4-d]pyridazine derivatives as well as their salts which are useful as effective and improved diuretics. Another object is to provide an industrially feasible method for the production of these novel compounds.

The pyrido[3,4-d]pyridazine derivatives of the present invention are those represented by the following general formula (I):

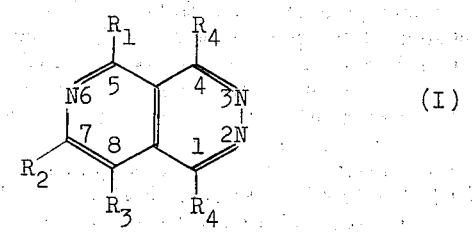

(wherein $R_1$ is hydrogen or a lower alkyl group of 1 to 4 carbon atoms; $R_2$ is an alkyl group of 1 to 4 carbon atoms, an aralkyl group of 7 to 8 carbon atoms or a substituted or unsubstituted phenyl, naphthyl, furyl or pyridyl, the substituent being a lower alkoxy group of 1 to 3 carbon atoms, a lower alkyl group of 1 to 3 carbon atoms, halogen or nitro; $R_3$ is hydrogen or a lower alkoxy group of 1 to 4 carbon atoms; and $R_4$ is a substituted or unsubstituted morpholino, piperidino or pyrrolidino, the substitutent being methyl or ethyl) and pharmaceutically acceptable salts thereof.

The alkyl group of 1 to 4 carbon atoms represented by $R_1$ and $R_2$ is exemplified by methyl, ethyl, n-propyl, i-propyl, n-butyl, i-butyl, s-butyl or t-butyl.

The aralkyl group represented by $R_2$ is exemplified by benzyl or phenethyl.

The lower alkoxy group of 1 to 4 carbon atoms represented by $R_3$ is exemplified by methoxy, ethoxy, n-propoxy, i-propoxy, n-butoxy, i-butoxy, s-butoxy or t-butoxy.

Referring to the substituent of the residue $R_2$, the alkoxy group of 1 to 3 carbon atoms is exemplified by methoxy, ethoxy, n-propoxy or i-propoxy; the alkyl group of 1 to 3 carbon atoms is exemplified by methyl, ethyl, n-propyl or i-propyl; and halogen is exemplified by chlorine, bromine, fluorine or iodine.

The residue $R_2$ and the residue $R_4$ may be substituted as mentioned above by one or more of substituents, preferably 1 to 2 substituents. When the residue $R_2$ or $R_4$ is substituted by not less than two substituents, the substituents may be the same with or different from one another.

The pharmaceutically acceptable salts of the compound (I) include the corresponding inorganic salts such as hydrochloric acid salt, sulfuric acid salt, nitric acid salt, phosphoric acid salt or the like as well as the corresponding organic acid salts such as oxalic acid salt, fumaric acid salt, tartaric acid salt, malic acid salt or the like.

The compound of the general formula (I) or its pharmaceutically acceptable salt is prepared by the following method which comprises reacting a compound shown by the general formula (II):

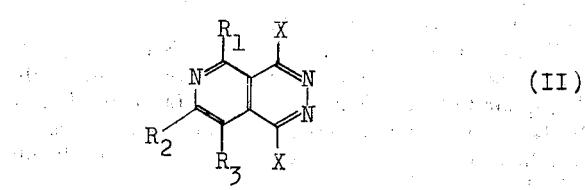

(wherein each of $R_1$, $R_2$ and $R_3$ has the same meaning as defined above; and X is halogen or a thio group), with a substituted or unsubstituted morpholine, piperidine or pyrrolidine, the substituent being methyl or ethyl.

The thio group to be eliminated by the above reaction is usually a residue represented by the general formula: $-S(O)mR$ in which $m$ is zero, one or two and R is a lower alkyl group of 1 to 3 carbon atoms, an aralkyl group of 7 to 8 carbon atoms such as benzyl or phenethyl or an aromatic group such as phenyl or tolyl.

The halogen represented by X is exemplified by chlorine, bromine, fluorine or iodine.

The starting compound of the general formula (II) in which X is halogen is prepared by for example a method which comprises reacting a compound shown by the general formula (IV) or (V):

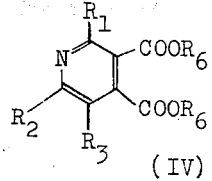 or 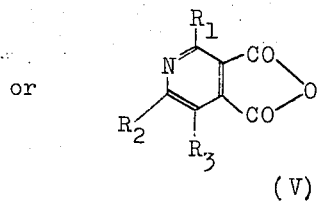

(wherein each of $R_1$, $R_2$ and $R_3$ has the same meaning as defined above, and $R_6$ is a lower alkyl group of 1 to 3 carbon atoms) with hydrazine to produce a compound shown by the general formula (VI):

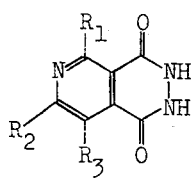

(VI)

(wherein each of $R_1$, $R_2$ and $R_3$ has the same meaning as defined above), reacting thus produced compound (VI) with phosphorus oxyhalide to produce a compound shown by the general formula (VII):

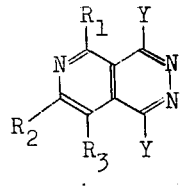

(VII)

(wherein each of $R_1$, $R_2$ and $R_3$ has the same meaning as defined above, and Y is halogen).

The starting compound (II) wherein X is a thio group is produced by a method which comprises reacting the compound of the general formula (VII) with a hydrosulfide metal compound such as sodium hydrosulfide to produce a compound shown by the general formula (VIII):

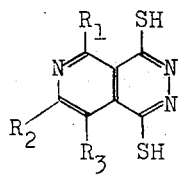

(VIII)

(wherein each of $R_1$, $R_2$ and $R_3$ has the same meaning as defined above) and reacting thus produced compound (VIII) with a compound shown by the general formula (IX):

RZ    (IX)

(wherein R has the same meaning as defined above, and Z is halogen or an aromatic sulfonyloxy group such as p-toluene-sulfonyloxy group) to produce a compound shown by the general formula (X):

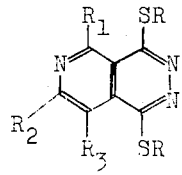

(X)

(wherein each of $R_1$, $R_2$, $R_3$ and R has the same meaning as defined above), and optionally reacting thus produced compound (X) with an oxidizing agent such as hydrogen peroxide, m-chloroperbenzoic acid, peracetic acid or the like to produce a compound shown by the general formula (XI) and/or (XII):

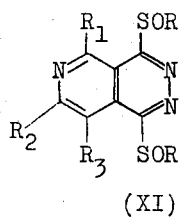 and/or 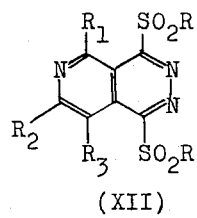

(XI)    (XII)

(wherein each of $R_1$, $R_2$, $R_3$ and R has the same meaning as defined above).

Referring to the method starting from the compound (II) wherein X is halogen, the reaction is carried out in the presence or absence of a reaction solvent. Any solvent which does not disturb the reaction may be employed and such a solvent is exemplified by alcohols such as methyl alcohol, ethyl alcohol, etc.; ethers such as tetrahydrofuran, ethyl ether, etc.; hydrocarbons and halogenated hydrocarbons such as benzene, chloroform, etc.; and esters such as ethyl acetate, etc. Further, to remove the hydrogen halide that will be by-produced in the course of the reaction, one may incorporate in the reaction system a suitable basic reagent (e.g. pyridine, N,N-dimethylaniline, etc.) as an acid acceptor.

The amount of the substituted or unsubstituted morpholine, piperidine or pyrrolidine relative to the compound of the general formula (II) is usually not less than 2 mols per mol of the compound (II). When the excess amount of the cyclic amine is employed, the cyclic amine may be served also as the reaction solvent as well as the acid acceptor.

The reaction temperature is usually in a range from −20°C to 300°C, preferably from 15°C to 150°C. The reaction is usually completed within a reaction period of time from 1 to 5 hours.

Referring to the method starting from the compound (II) wherein X is a thio group, the reaction conditions may be the same as in the method starting from the compound wherein X is halogen. But in this case, it is advisable for the purpose of a higher yield that the reaction is carried out under an elevated pressure from 1 atms.G to 100 atms.G at a temperature from 20°C to 300°C, most preferably from 50°C to 250°C.

After the reaction, the reaction product is normally recovered from the reaction mixture in the form of a free base in accordance with conventional means such as concentration, crystallization, chromatography or the like. Of course, the reaction product of free basic form may be converted into the above-mentioned pharmaceutically acceptable salt by a per se known means.

The objective compounds of the general formula (I) as well as pharmaceutically acceptable salts thereof have effective diuretic action. In more detail, the present compounds have the following properties.

1. The compounds of this invention have effective and strong diuretic action.
2. They show extremely low toxicity.
3. They induce urinary excretion of a large amount of sodium ion, but induce urinary excretion of relatively small amount of potassium ion which is an essential element to the human body. Thus, the excretion ratio of urinary $Na^+/K^+$ is comparatively high in the present compounds.

4. The present compounds can produce a marked additional diuretic response in the animal undergoing maximum diuresis with known diuretics. This fact suggests that the mechanism of diuretic action of the present compounds is different from those of known diuretics. Thus, combination of the present compounds with other known diuretics can produce much increased diuretic effect.

Therefore, the compounds of the present invention can be used as diuretics and are administered for the purpose per se or in the form of a pharmaceutically acceptable composition in admixture with a suitable and conventional carrier or adjuvant.

The pharmaceutical composition may take the form of tablets, granules, powders, capsules, injections and may be administered orally or parenterally.

Usual daily doses of the compounds lie in the range of about 10 to about 200 milligrams per human adult upon oral administration or of about 5 to 100 milligrams parenteral administration.

For further explanation of the present invention, following Examples are given wherein the word "part(s) by weight" has the same relationahip to "part(s) by volume" as do "gram(s)" to "milliliter(s)".

Preparation of Starting Materials

1. Production of 1,4-dichloro-7-(p-methoxyphenyl)-5-methyl-pyrido[3,4-d]pyridazine 10 parts by weight of 3,4-diethoxycarbonyl-6-(p-methoxyphenyl)-2-methylpyridine is incorporated into 40 parts by volume of hydrazine hydrate, and the resulting mixture is refluxed for three hours. The precipitated crystals are collected by filtration, washed with ethanol and suspended in 100 parts by volume of water. The mixture is acidified by the addition of acetic acid to obtain 1,2,3,4-tetrahydro-7-(p-methoxyphenyl)-5-methyl-1,4-dioxopyrido[3,4-d]pyridazine as colorless fine crystals. A mixture is made of 3.0 parts by weight of the fine crystals, 45 parts by volume of phosphorus oxychloride and 4.5 parts by volume of N,N-dimethylaniline. The mixture is heated at temperature ranging from 90° to 100°C for three hours. Then, the reaction mixture is left standing at room temperature overnight. The precipitated crystals are collected by filtration, washed with ether, recrystallized from chloroform to obtain the desired compounds melting at 214° to 219°C (decomposition) as pale yellow needles.

2. Production of 1,4-dimethylmercapto-7-phenyl-pyrido[3,4-d]pyridazine

Potassium hydrosulfide methanolic solution is prepared by reacting 7 parts by weight of potassium hydroxide, 150 parts by volume of methanol and hydrogen sulfide gas in accordance with the known method. 4.2 parts by weight of 1,4-dichloro-7-phenyl-pyrido[3,4-d]pyridazine is added to the potassium hydrosulfide solution, and the resulting mixture is stirred at room temperature for three hours. Methanol is evaporated under reduced pressure, and the residue is added to 50 parts by volume of water to obtain a solution. The solution is acidified by the addition of acetic acid to precipitate yellow crystals. The crystals are collected by filtration, washed with water and dried to obtain 1,4-dimercapto-7-phenyl-pyrido[3,4-d]pyridazine melting at 212° to 215°C (decomposition).

3.0 parts by weight of thus prepared compound is added to 220 parts by volume of a 10% sodium hydroxide aqueous solution, followed by the addition of 3.7 parts by weight of methyl iodide. The mixture is stirred for three hours at room temperature to precipitate crystals. The crystals are recrystallized from ethanol to obtain 1,4-dimethylmercapto-7-phenylpyrido[3,4-d]pyridazine as colorless needles melting at 155°C.

EXAMPLE 1

0.5 part by weight of 1,4-dichloro-7-methyl-8-methoxypyrido[3,4-d]pyridazine and 3.6 parts by weight of morpholine are heated together at 80°C for 1.5 hour and, then, the excess morpholine is distilled off. To the residue is added water, whereupon an oily precipitate is obtained. This oil is triturated with a small amount of methanol to obtain crystals of 7-methyl-8-methoxy-1,4-dimorpholinopyrido[3,4-d]pyridazine. Recrystallization from a mixture of methanol and water (1:3) yields crystals melting at 145°–146°C. Yield 0.5 part by weight.

Elementary analysis for $C_{17}H_{24}O_3N_5$: Calcd. C, 59.11; H, 6.71; N, 20.28; Found C, 59.10; H, 6.81; N, 20.09

In accordance with a similar manner as described in Example 1, the following compounds are obtained.

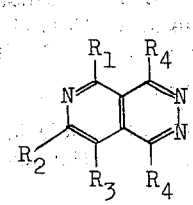

| $R_1$ | $R_2$ | $R_3$ | $R_4$ | Melting point (°C) and appearance | Elementary analysis (%) | Yield(%) |
|---|---|---|---|---|---|---|
| H | $-CH_3$ | $-OCH_3$ | $-N\bigcirc$ | 109 to 110°C pale yellow needles | Calcd. C,66.83;H,7.97; N,20.51<br>Found C,66.58;H,7.75; N,20.31 | 62 |
| H | $-\bigcirc$ | H | $-N\bigcirc O$ | 158 to 172°C pale brown fine granules | Calcd. C,66.82;H,6.14; N,18.56<br>Found C,66.64;H,5.74; N,17.53 | 80 |

| $R_1$ | $R_2$ | $R_3$ | $R_4$ | Melting point (°C) and appearance | Elementary analysis (%) | Yield(%) |
|---|---|---|---|---|---|---|
| H | -⌬ | H | -N◯O | 183°C pale yellow fine granules | Calcd. C,67.50;H,6.44; N,17.89<br>Found C,67.38;H,6.43; N,17.61 | 82 |
| H | -⌬ | H | -N◯ | 149 to 150°C yellow plates | Calcd. C,73.96;H,7.29; N,18.75<br>Found C,73.85;H,7.31; N,19.00 | 80 |
| H | -CH$_2$-⌬ | -OCH$_3$ | -N◯O | 174 to 175°C pale yellow flakes | Calcd. C,65.54;H,6.46; N,16.62<br>Found C,65.32;H,6.22; N,16.68 | 72 |
| H | -CH$_2$-CH(CH$_3$)$_2$ | -OCH$_3$ | -N◯O | 123°C yellow needles | Calcd. C,61.99;H,7.54; N,18.08<br>Found C,61.99;H,7.51; N,18.02 | 80 |

EXAMPLE 2

2.0 parts by weight of 1,4-dichloro-7-phenyl-pyrido[3,4-d]pyridazine is added to 20 parts by volume of 2-methylmorpholine, and the resulting mixture is heated at 130° to 140°C for four hours. The excess amount of 2-methylmorpholine is removed by evaporation under reduced pressure. Water is added to the residue to obtain crude crystals, which is recrystallized from n-hexane to obtain 1,4-bis(2'-methylmorpholino)-7-phenylpyrido[3,4-d]pyridazine as yellow prisms melting at 75° to 81°C.

Elementary analysis for $C_{23}H_{27}O_2N_5$: Calcd. C, 68.12; H, 6.71; N, 17.27; Found C, 68.26; H, 6.95; N, 16.98

In the above method, the same amount of 2,6-dimethylmorpholine is employed in the place of 2-methylmorpholine to obtain 1,4-bis(2',6'-dimethylmorpholino)-7-phenylpyrido[3,4-d]pyridazine melting at 248° to 250°C as yellow fine needles.

Elementary analysis for $C_{25}H_{31}O_2N_5$: Calcd. C, 69.25; H, 7.21; N, 16.16; Found C, 69.25; H, 7.17; N, 16.19

EXAMPLE 3

1.0 part by weight of 1,4-dichloro-7-(p-methoxyphenyl)-5-methylpyrido[3,4-d]pyridazine is added to 10 parts by volume of morpholine, and the resulting mixture is heated at 130°C for 3 hours. The excess amount of morpholine is removed by evaporating under reduced pressure, and water is added to the residue. The crude crystals are collected by filtration and recrystallized from ethanol to obtain 7-(p-methoxyphenyl)-5-methyl-1,4-dimorpholinopyrido[3,4-d]pyridazine as gray prisms melting at 206° to 209°C.

Elementary analysis for $C_{23}H_{27}O_3N_5$: Calcd. C, 65.54; H, 6.46; N, 16.42; Found C, 65.42; H, 6.26; N, 16.55

The following compounds of the general formula:

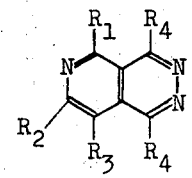

are prepared by the similar manner as in the above process.

| $R_1$ | $R_2$ | $R_3$ | $R_4$ | Melting point (°C) and appearance | Elementary analysis (%) |
|---|---|---|---|---|---|
| -CH$_3$ | CH$_3$-⌬ | H | -N◯O | 222 to 224°C pale yellow needles | Calcd. C,68.12;H,6.71; N,17.27<br>Found C,67.83;H,6.75; N,17.49 |
| -CH$_3$ | CH$_3$O-⌬ | H | -N◯ | 174 to 176°C yellowish orange needles | Calcd. C,71.91;H,7.48; N,16.77<br>Found C,71.95;H,7.22; N,16.54 |
| -CH$_3$ | ⌬O (furyl) | H | -N◯O | 163 to 164°C yellow granules | Calcd. C,62.98;H,6.08; N,18.36<br>Found C,63.52;H,6.00; N,18.03 |

-continued

| $R_1$ | $R_2$ | $R_3$ | $R_4$ | Melting point (°C) and appearance | Elementary analysis (%) |
|---|---|---|---|---|---|
| $-CH_3$ | $O_2N-C_6H_4-$ (NO2-phenyl) | H | -N◯O (morpholino) | 218°C brown crystals | Calcd. C,60.54;H,5.54; N,19.26 Found C,60.12;H,5.39; N,18.70 |
| $-CH_3$ | Cl-C_6H_4- (4-Cl-phenyl) | H | -N◯O | 246 to 274°C yellow needles | Calcd. C,62.04;H,5.68; N,16.44;Cl,8.32 Found C,62.14;H,5.68; N,16.24;Cl,8.93 |
| $-CH_3$ | Cl-C_6H_4- (3-Cl-phenyl) | H | -N◯O | 184 to 186°C yellow needles | Calcd. C,62.04;H,5.68; N,16.44;Cl,8.32 Found C,62.10;H,5.66; N,16.43;Cl,8.33 |
| H | Cl-C_6H_4- (4-Cl-phenyl) | H | -N◯O | 217 to 221°C yellow powders | Calcd. C,61.23;H,5.38; N,17.01;Cl,8.61 Found C,61.15;H,5.54; N,16.81;Cl,8.68 |
| H | Cl-C_6H_4- (3-Cl-phenyl) | H | -N◯O | 179 to 180°C yellow needles | Calcd. C,61.23;H,5.38; N,17.01;Cl,8.61 Found C,61.12;H,5.50; N,16.85;Cl, 8.55 |
| $-CH_3$ | pyridyl | H | -N◯O | 221 to 224°C yellow needles | Calcd. C,64.27;H,6.16; N,21.42 Found C,64.15;H,6.00; N,21.33 |

EXAMPLE 4

1 part by weight of 1,4-dimethylmercapto-7-phenylpyrido[3,4-d]pyridazine and 10 parts by volume of morpholine are placed in a glass tube, and the glass tube is sealed. The reaction system is heated at 180°C for 8 hours. The excess amount of morpholine is removed by evaporating under reduced pressure, and water is added to the residue. Thus precipitated crude crystals are collected by filtration. The crude crystals are adsorbed on a column packed with silica-gel, followed by eluting with a mixture of acetone and benzene (1:4). The eluate is concentrated under reduced pressure and recrystallized from methanol to obtain 1,4-dimorpholino-7-phenylpyrido[3,4-d]pyridazine as pale yellow needles melting at 186° to 188°C.

EXAMPLE 5

One part by weight of 1,4-dimorpholino-7-phenylpyrido[3,4-d]pyridazine is dissolved in 50 parts by volume of ethanol under warming. Ten parts by volume of a 10% hydrogen chloride ethanolic solution is added to the solution and the resulting mixture is cooled to precipitate 1,4-dimorpholino-7-phenylpyrido[3,4-d]pyridazine hydrochloride. The product (one part by weight) is collected by filtration and recrystallized from 50 parts by volume of ethanol to obtain highly purities 1,4-dimorpholino-7-phenylpyrido[3,4-d]pyridazine hydrochloride melting at 176 to 181°C as orange needles.

Elementary analysis for $C_{21}H_{24}O_2N_5CL$: Calcd. C,60.93; H, 5.84; N, 16.92; Found C,60.74; H, 5.70; N, 16.72

EXAMPLE 6

In a similar manner as described in Example 1, the following pyrido[3,4-d]pyridazine derivatives of the general formula:

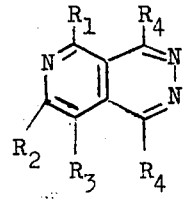

| $R_1$ | $R_2$ | $R_3$ | $R_4$ | Melting point (°C) and appearance | Elementary analysis (%) |
|---|---|---|---|---|---|
| H | -C_6H_5 | H | -N◯ (pyrrolidino) | 130 to 131°C orange plates | Calcd. C,73.01;H,6.71; N,20.28 Found C,72.90;H,6.62; N,19.96 |
| H | $-CH_3$ | $-OC_4H_9$ (n) | -N◯O | 108 to 110°C pale brown needles | Calcd. C,61.99;H,7.54; N,18.08 Found C,61.85;H,7.58; N,17.95 |

What is claimed is:

1. A pyrido [3,4-d]pyridazine derivative shown by the general formula:

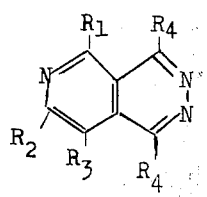

wherein $R_1$ is hydrogen or an alkyl group of 1 to 3 carbon atoms; $R_2$ is an alkyl group of 1 to 4 carbon atoms, phenyl, naphthyl, benzyl or phenethyl; $R_3$ is hydrogen or an alkoxy group of 1 to 3 carbon atoms; and $R_4$ is morpholino, piperidino or pyrrolidino and a pharmaceutically acceptable salt thereof.

2. The pyrido[3,4-d]pyridazine derivative as claimed in claim 1, wherein $R_1$ is hydrogen.

3. The pyrido[3,4-d]pyridazine derivative as claimed in claim 1, wherein $R_1$ is hydrogen and $R_2$ is phenyl.

4. The pyrido[3,4-d]pyridazine derivative as claimed in claim 1, wherein $R_1$ is hydrogen and $R_3$ is hydrogen.

5. The pyrido[3,4-d]pyridazine derivative as claimed in claim 1, wherein $R_1$ is hydrogen and $R_3$ is an alkoxy group of 1 to 3 carbon atoms.

6. The pyrido[3,4-d]pyridazine derivative as claimed in claim 1, wherein $R_1$ is hydrogen and $R_4$ is morpholino.

7. The pyrido[3,4-d]pyridazine derivative as claimed in claim 1, wherein $R_1$ is hydrogen, $R_2$ is phenyl, $R_3$ is hydrogen and $R_4$ is morpholino.

8. The pyrido[3,4-d]pyridazine derivative as claimed in claim 1, wherein $R_1$ is hydrogen, $R_2$ is methyl, $R_3$ is methoxy and $R_4$ is morpholino.

* * * * *